(12) United States Patent
Rossini

(10) Patent No.: US 7,611,119 B2
(45) Date of Patent: Nov. 3, 2009

(54) LAPTOP COMPUTER STAND

(76) Inventor: Alfred P. Rossini, 1 Wyndemere Dr., Southborough, MA (US) 01772

( * ) Notice: Subject to any disclaimer, the term of this patent is extended or adjusted under 35 U.S.C. 154(b) by 0 days.

(21) Appl. No.: 11/836,830

(22) Filed: Aug. 10, 2007

(65) Prior Publication Data

US 2008/0035823 A1 Feb. 14, 2008

Related U.S. Application Data

(63) Continuation of application No. 10/927,700, filed on Aug. 27, 2004, now abandoned.

(60) Provisional application No. 60/498,051, filed on Aug. 27, 2003.

(51) Int. Cl.
F16M 13/00 (2006.01)

(52) U.S. Cl. .......................... 248/551; 248/552; 70/58

(58) Field of Classification Search ................ 248/551, 248/918, 552, 441.1, 553, 453, 126, 346.01, 248/917; 312/231, 233; 108/42, 50.1; 70/58, 70/57.1, 57, 16
See application file for complete search history.

(56) References Cited

U.S. PATENT DOCUMENTS

| | | | |
|---|---|---|---|
| 3,391,256 A * | 7/1968 | Nawman | 379/445 |
| 3,744,282 A * | 7/1973 | Hemphill | 70/58 |
| 4,005,279 A * | 1/1977 | Richter | 379/445 |
| 4,453,692 A * | 6/1984 | LeDoux et al. | 248/552 |
| 4,471,409 A * | 9/1984 | Dittrich | 361/683 |
| 4,696,449 A | 9/1987 | Woo et al. | |
| 4,750,204 A * | 6/1988 | Bartley et al. | 379/445 |
| 4,937,860 A * | 6/1990 | Smith | 379/445 |
| 4,946,120 A * | 8/1990 | Hatcher | 248/183.2 |
| 5,052,651 A | 10/1991 | Guddee | |
| 5,085,395 A | 2/1992 | Frater et al. | |
| 5,595,074 A | 1/1997 | Munro | |
| 5,645,261 A | 7/1997 | Glynn | |
| 5,673,628 A * | 10/1997 | Boos | 108/44 |
| 5,709,110 A * | 1/1998 | Greenfield et al. | 70/58 |
| 5,769,369 A | 6/1998 | Meinel | |
| 5,794,463 A * | 8/1998 | McDaid | 70/18 |
| 5,836,183 A * | 11/1998 | Derman | 70/58 |
| 5,859,762 A | 1/1999 | Clark et al. | |
| 5,941,180 A * | 8/1999 | Becker | 108/77 |
| 6,021,720 A | 2/2000 | Boos et al. | |
| 6,216,499 B1 | 4/2001 | Ronberg et al. | |
| 6,237,375 B1 * | 5/2001 | Wymer | 70/14 |
| 6,443,417 B2 | 9/2002 | Galant | |
| 6,491,268 B1 | 12/2002 | Channer et al. | |
| 6,491,276 B1 * | 12/2002 | Belliveau | 248/372.1 |
| 6,585,212 B2 * | 7/2003 | Carnevali | 248/346.07 |
| 6,711,921 B1 | 3/2004 | Yang | |
| 6,763,690 B2 | 7/2004 | Galant | |
| 7,007,912 B1 | 3/2006 | Giuliani et al. | |
| 7,315,443 B2 * | 1/2008 | Allen | 361/683 |
| 2004/0007651 A1 * | 1/2004 | Williams et al. | 248/346.06 |
| 2004/0177658 A1 * | 9/2004 | Mitchell | 70/58 |

* cited by examiner

Primary Examiner—Kimberly T. Wood
(74) Attorney, Agent, or Firm—Brian M. Dingman; Mirick, O'Connell, DeMallie & Lougee, LLP

(57) ABSTRACT

A laptop computer stand, for holding a laptop computer having a keyboard portion and a display portion that is pivotable relative to the keyboard portion. The stand has a base adapted to either sit on a surface or be coupled to a structure, and a support member coupled to the base, wherein the laptop keyboard portion sits on the support member. The support member has a retaining structure that overlies at least part of the laptop keyboard portion, to retain the keyboard portion on the support member. The stand also has a locking mechanism coupled to the base or the support member, and selectively fixable to the laptop computer.

2 Claims, 6 Drawing Sheets

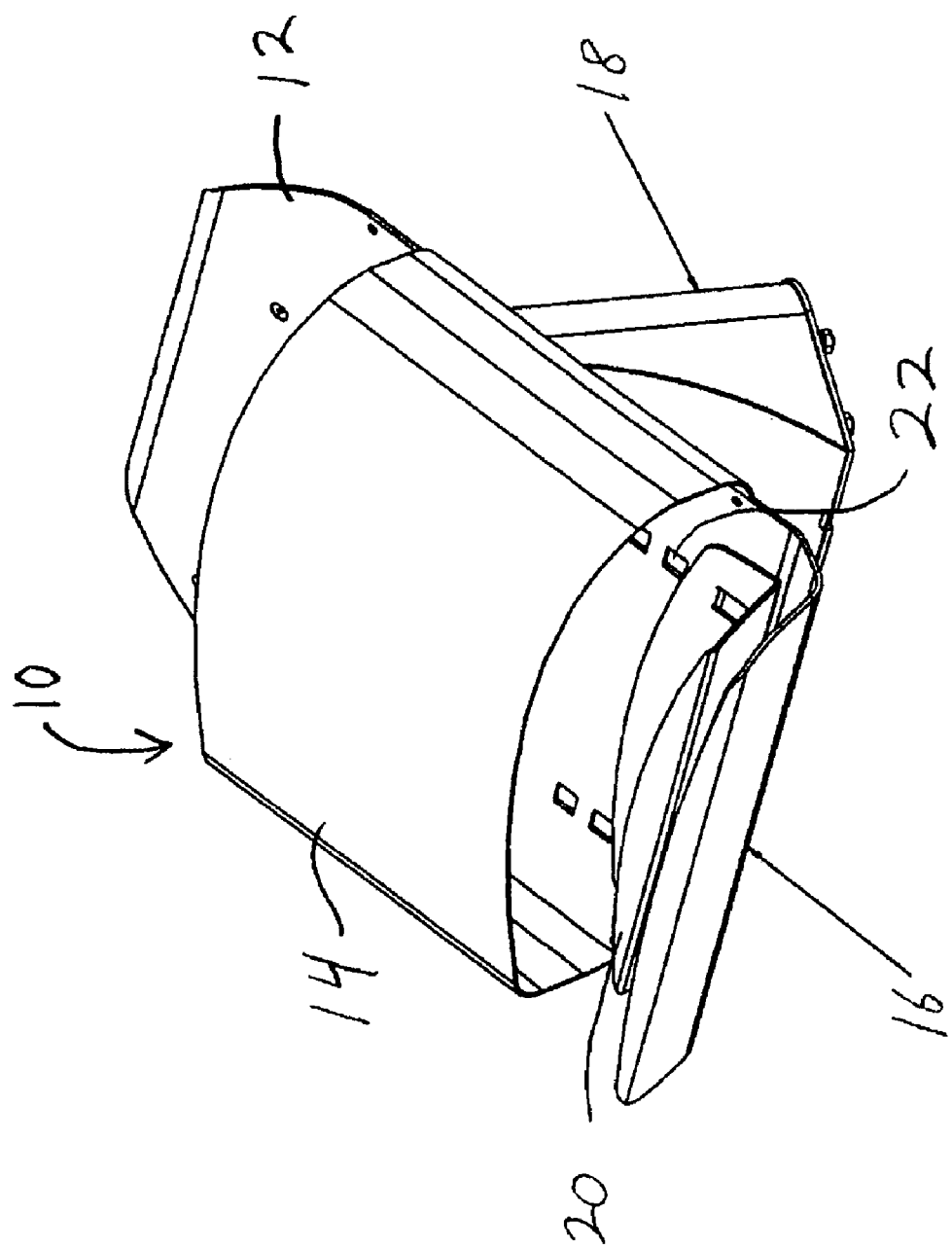

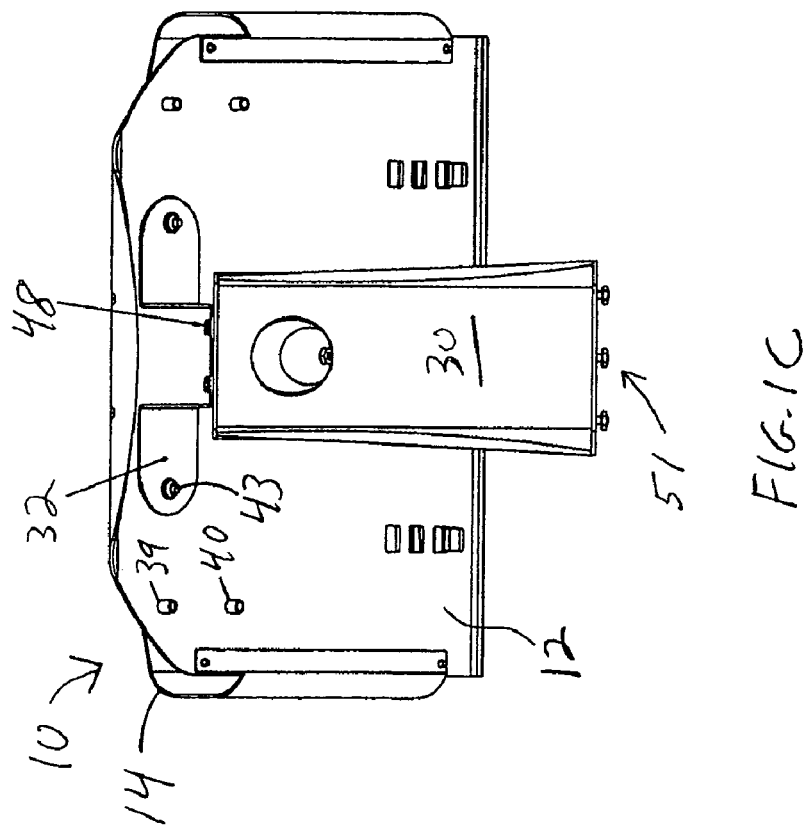
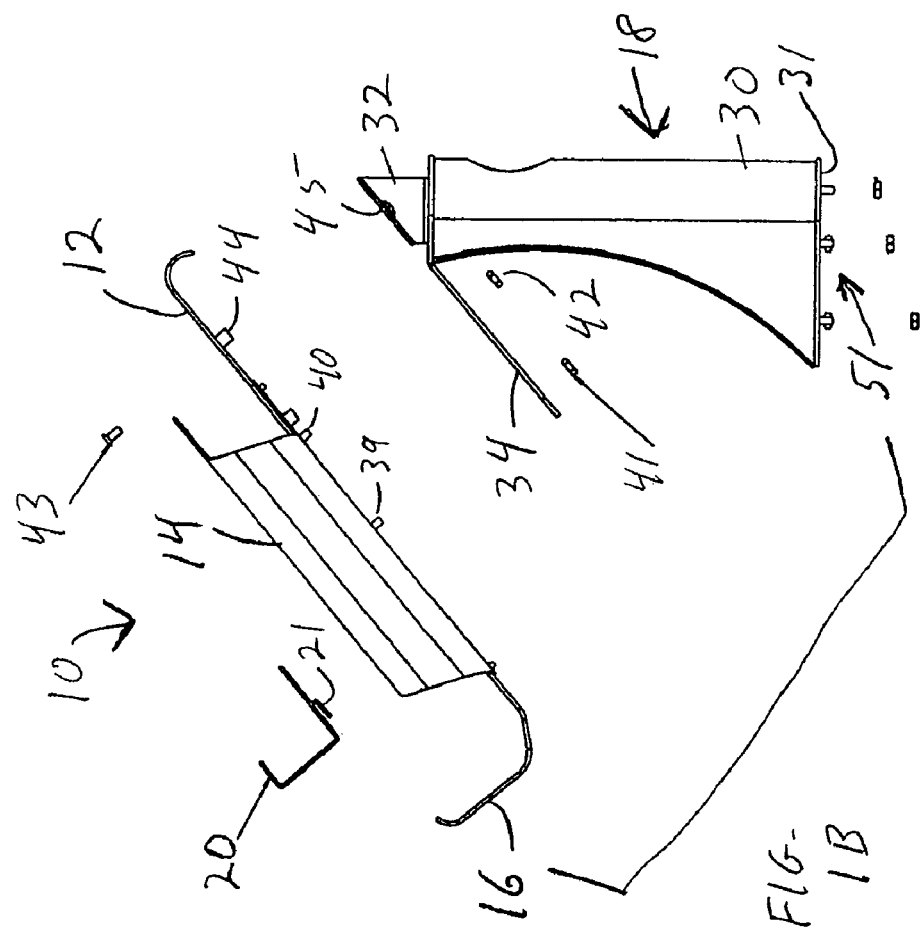
FIG. 1C
FIG. 1B

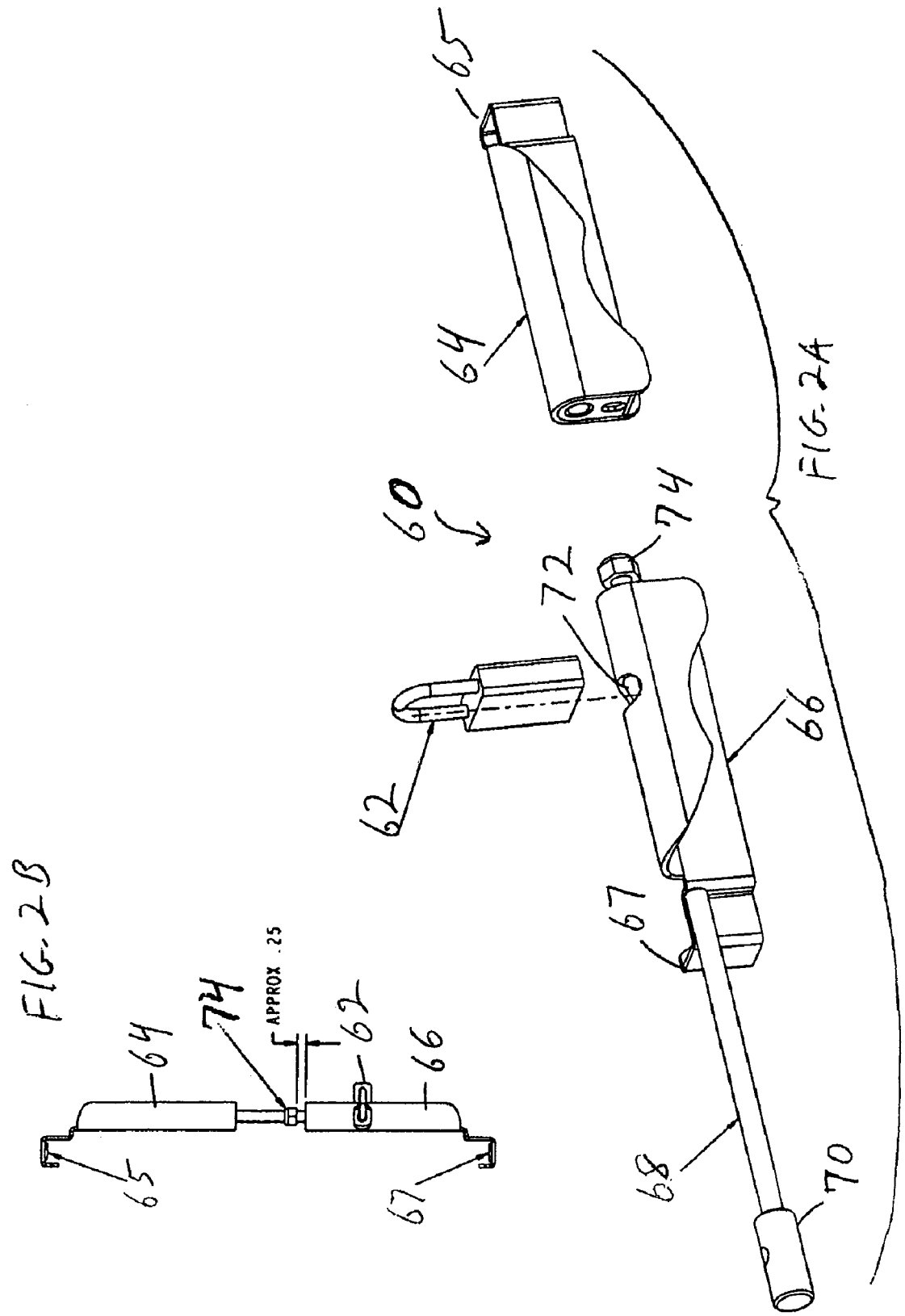

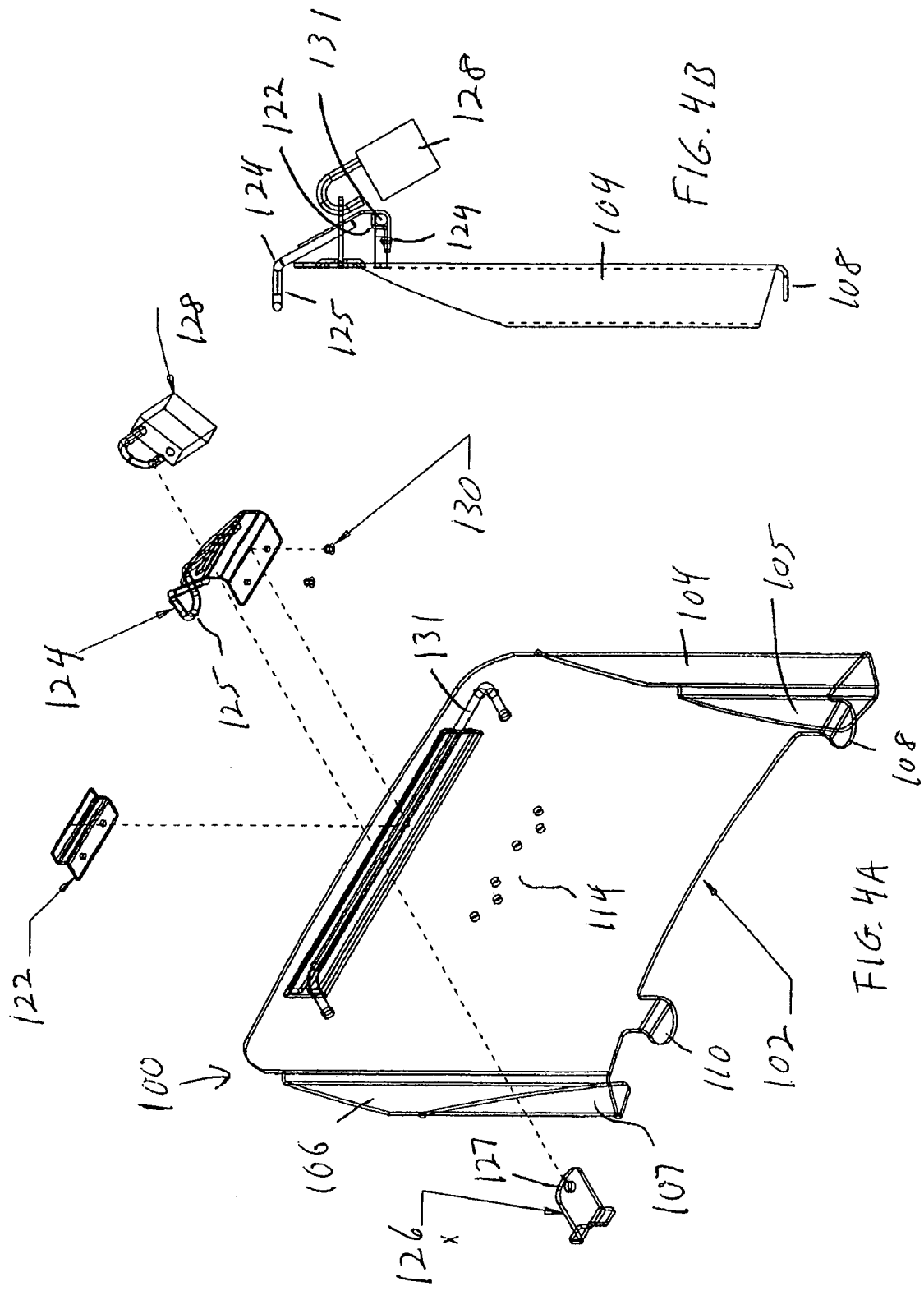

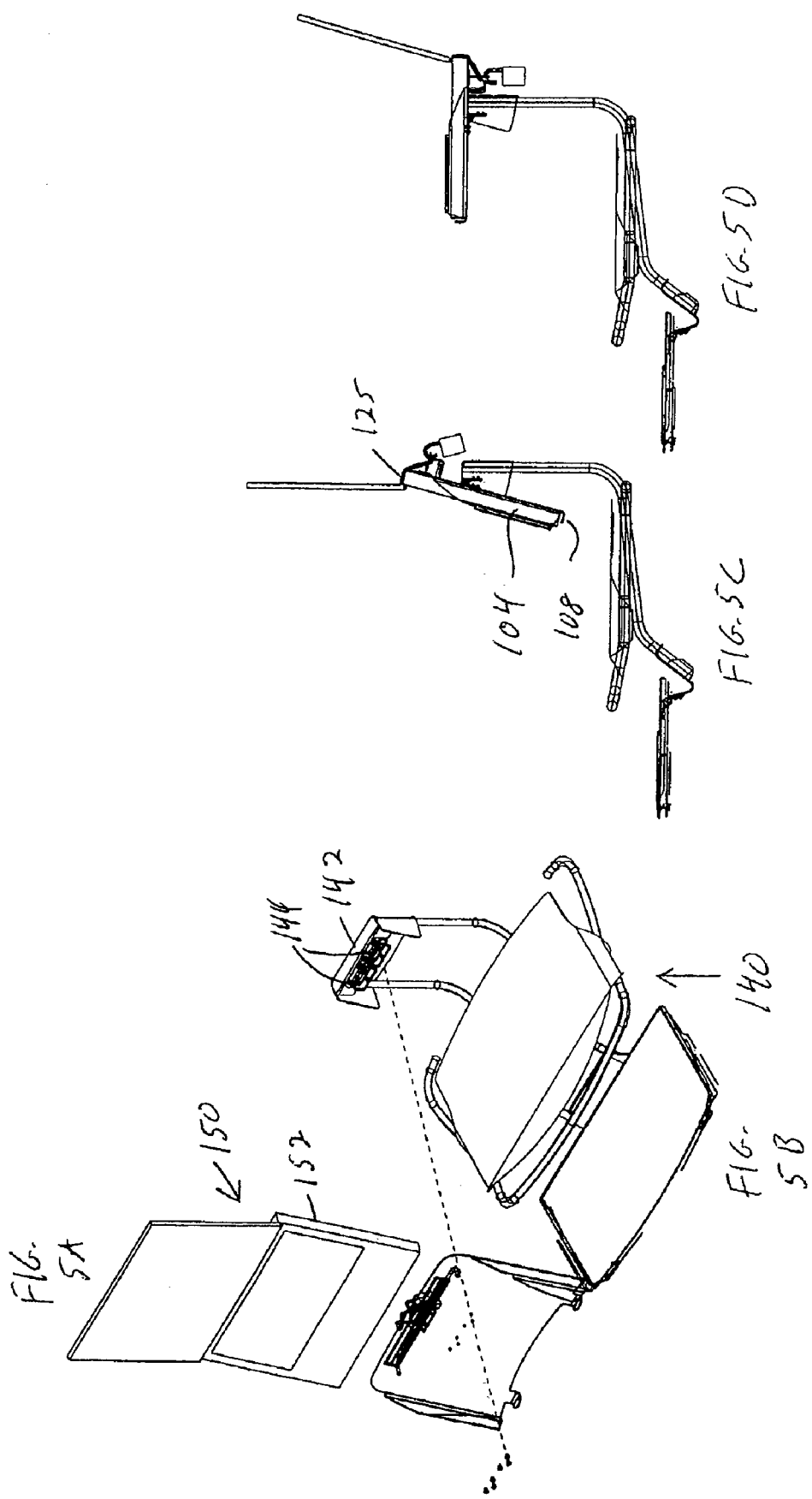

LAPTOP COMPUTER STAND

CROSS REFERENCE TO RELATED APPLICATION

This application is a continuation of U.S. patent application Ser. No. 10/927,700, filed Aug. 27, 2004 now abandoned, which is based upon and claims the priority of the same applicant's U.S. Provisional application of the same title filed Aug. 27, 2003, Application No. 60/498,051, the entire disclosure of which is incorporated herein by reference.

FIELD OF THE INVENTION

This invention relates to a stand that supports and secures a laptop computer.

BACKGROUND OF THE INVENTION

Mobile carts used as workstations are known. These carts are commonly used in medical facilities and on manufacturing floors. They are typically adapted to carry a computer, and usually have additional shelf space available for the user, for such things as paper work, medications, and/or portable medical equipment.

These carts are typically used by many different people over the course of a day or a week. It is thus important that these carts have certain functional and ergonomic features. For example, for carts that are adapted for the use of a laptop computer, it is desirable for the laptop to be securely held in place, yet accessible for viewing and use while held on the cart. It is typically also important for the display portion of the computer to be adjustable for optimal viewing. Further, it is imperative that there be some facility for locking the laptop while it is held in the use position, so that theft is deterred.

Beyond carts, there are many uses of a laptop computer stand that adjustably maintains the laptop in a position in which it can be used, and comfortably viewed, by a user, yet is secured from theft.

SUMMARY OF THE INVENTION

This invention features a laptop computer stand, for holding a laptop computer having a keyboard portion and a display portion that is pivotable relative to the keyboard portion, the stand comprising a base adapted to either sit on a surface or be coupled to a structure, and a support member coupled to the base, wherein the laptop keyboard portion sits on the support member, the support member comprising a retaining structure that overlies at least part of the laptop keyboard portion, to retain the keyboard portion on the support member. There is a locking mechanism coupled to the base or the support member, and selectively fixable to the laptop computer.

The invention may further include one or more of the following features. The support member may comprise a support plate on which the laptop keyboard portion sits. The support plate may be tilted at an angle from the horizontal. The support member may be tiltable relative to the base. The laptop computer stand may further comprise a lower support plate coupled to the support plate. The lower support plate may support the lower edge of the laptop keyboard portion. The lower support plate may be adjustably received in the support plate.

The retaining structure may overly the entire width of the laptop keyboard portion, or only the edges of the laptop keyboard portion. The locking mechanism may comprise separable parts. The parts may be receivable into one another to mechanically couple them together. The mechanical coupling may be accomplished with mating threads. The locking mechanism may further comprise brackets that releasably grip opposite sides of the laptop computer. The opposite sides may be of the display portion of the laptop computer. The locking mechanism may further comprise a padlock that is insertable through one of the separable parts. The padlock, when inserted, prevents the separation of the separable parts. The laptop computer stand may further comprise a cable that couples the locking mechanism to another part of the stand.

Also featured in the invention is a laptop computer stand, for holding a laptop computer having a keyboard portion and a display portion that is pivotable relative to the keyboard portion, the stand comprising a base adapted to either sit on a surface or be coupled to a structure, a support member comprising a support plate coupled to the base, wherein the laptop keyboard portion sits on the support plate, the support member further comprising a retaining structure that overlies at least part of opposite edges of the laptop keyboard portion, to retain the keyboard portion on the support member. There is a locking mechanism coupled to the base or the support member, and selectively fixable to the laptop computer, the locking mechanism comprising two separable parts that can be mechanically coupled together and locked in the coupled position, each such part carrying a structure that releasably grips an edge of the laptop computer.

BRIEF DESCRIPTION OF THE DRAWINGS

Other objects, features and advantages will occur to those skilled in the art from the following description of the preferred embodiments and the accompanying drawings in which:

FIGS. 1A through 1C are perspective, exploded and rear views, respectively, of one preferred embodiment of the laptop computer stand of this invention;

FIGS. 2A and 2B are separated and assembled views, respectively, of a locking mechanism for the embodiment of FIGS. 1A-1C;

FIG. 4A is an exploded view and 4B a side view of an alternative preferred embodiment of the invention;

FIG. 5A shows a laptop being inserted into the embodiment of FIGS. 4A and 4B;

FIG. 5B shows the top section of a mobile cart on which the stand of the invention can be mounted: and FIGS. 5C and 5D are side views of the stand of FIGS. 4A and 4B mounted on the section of the mobile cart shown in FIG. 5B.

DESCRIPTION OF THE PREFERRED EMBODIMENTS

Figure 3:
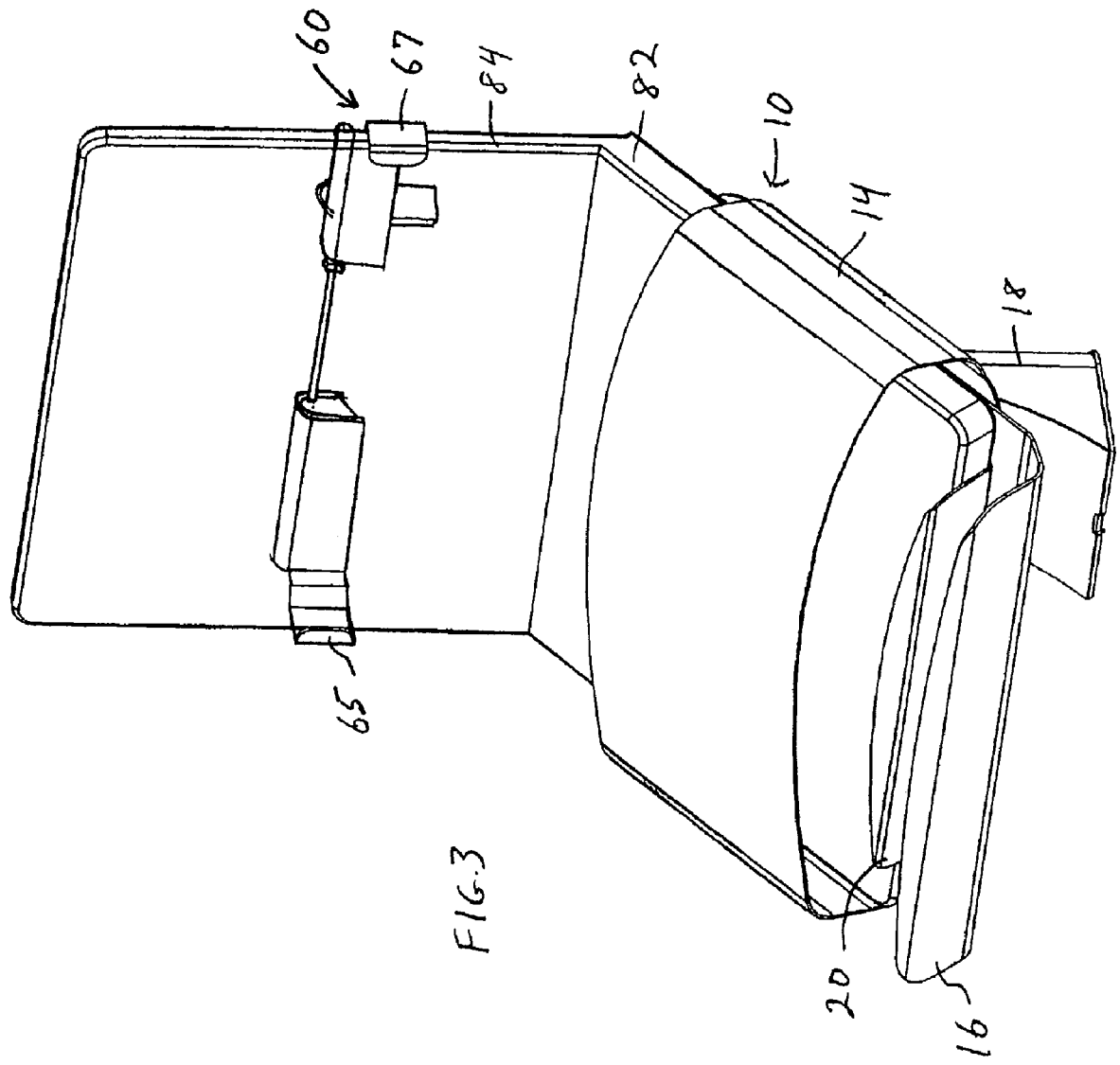
FIG. 3 shows the combination of the stand of FIGS. 1A-1C and locking mechanism of FIGS. 2A and 2B to accomplish a locking stand system.

This invention comprises a stand for laptop computers. The stand raises the height of the laptop and holds it at a convenient angle. The stand can be free-standing, or can be mounted to a base such as a table, desk, or moveable cart.

The preferred embodiment of the invention is shown in FIGS. 1A-1C. An optional locking mechanism that prevents the laptop computer from being removed from the stand is shown in FIGS. 2A and 2B. The combination of the stand and locking mechanism to accomplish a locking stand system is shown in FIG. 3. An alternative preferred embodiment of the invention is shown in FIG. 4.

Stand 10 comprises angled support member 12 that is held by base 18. Base 18 can be adapted to sit on a horizontal surface or be attached another structure, as further explained below. Overlying retainer member 14 along with member 12 creates a surround that defines a cavity into which the keyboard portion of a laptop computer is placed. Lower support plate 16 provides an area against which the lower (keyboard) portion of the laptop rests. Adjustable auxiliary plate 20, against which the bottom edge of the laptop rests, may be included so that the device can accommodate different size laptops, or to provide additional adjustability. Plate 20 is adjustable to a number of positions relative to member 12 to move the bottom laptop support area up-and-down as desired, using a slot 22 and insertable tab 21 arrangement.

Stand 10 is shown in exploded view in FIG. 1B and rear view in FIG. 1C. Base 18 includes base member 30 with lower surface 31 that may be placed on a table, desk or the like. Alternatively, coupling studs and nuts assembly 51 may project from the bottom of surface 31 to allow the device to be bolted to a mobile cart, desk or the like.

Member 12 is coupled to member 30 through bracket 32 and fasteners 43 that pass through openings 44 and are received in nuts 45. Projecting studs such as studs 39 and 40 pass through cantilevered plate 34 and are held therein with nuts 41 and 42, respectively.

Locking mechanism 60 is shown in FIGS. 2A and 2B and comprises separable members 64 and 66 that can be mechanically coupled together and then prevented from separation by inserting lock 62 in opening 72. Threaded rod 68 with end member 70 passes through an opening in member 66 and threads into an insert that is fastened to member 64. End member 70 can be gripped and rotated, which causes member 64 to pull in toward member 66. This causes C-shaped end brackets 65 and 67 to overlap and releasably couple to opposite sides of the laptop display 84, as shown in FIG. 3. Once lock 62 is inserted, rod 68 cannot be rotated, so locking mechanism 60 cannot be removed from the laptop. A cable (not shown) can be looped through openings in members 64 and 66 and through openings in member 10 (not shown), with the cable ends crimped, to prevent removal of the locking mechanism from the laptop computer. As a result, mechanism 60 prevents the laptop from being removed from stand 10. If stand 10 is fixed to a larger structure, this increases the security of a laptop computer held in the inventive stand.

An alternative embodiment of the inventive stand 100 is shown in FIGS. 4A and 4B. Stand 100 has support member 102 with integral side members 104 and 106, having keyboard-overlaying portions 105 and 107, respectively. Portions 105 and 107 overly only a small portion of each side of the laptop keyboard portion. This allows the user to access the keys, mouse control functions, and other functional aspects located on the top side of the keyboard portion, so that the laptop can be used in a normal fashion while being supported by and retained by the inventive stand. Lower integral tabs 108 and 110 support the lowermost edge of the laptop, while overlying upper tab 125 of sliding retaining member 124 lies against or very close to the top edge of the keyboard portion. This arrangement prevents the keyboard portion from being lifted off of member 102 when tab 125 is in place. As explained in more detail below, padlock 128 holds member 124 in place, which effectively locks the laptop in the stand.

Member 122 is coupled to member 124 such that they mount on rear bar 131. This allows tab 125 to be slid left and right relative to the laptop. When the laptop is placed on the stand (as shown in FIG. 5A, tab 125 is slid to the side. It is then slid back in place to the middle. Tab 126 fits through member 124 such that opening 127 of tab 126 is accessible. Padlock 128 is then placed through opening 127, which effectively locks tab 125 in place over the end of the laptop keyboard portion. The laptop is now held by and secured by the stand.

Stand 100 is preferably constructed such that it is pivotable relative to the structure to which it is coupled. In the example shown in FIGS. 5B-5D, this structure is the top portion of a mobile laptop computer stand such as the Z cart available from JACO, Inc. of Franklin, Mass. Pivoting can be accomplished by using continuous torque hinges 144 on fixed member 142, that are coupled to the stand through openings 114 in support member 102. These hinges are preferably arranged such that the laptop is pivotable from an almost vertical position shown in FIG. 5C, to a horizontal position shown in FIG. 5D. This allows both the keyboard portion and the display portion of the laptop to be placed at a desired angle. The cart has inherent height adjustment, which thus accomplishes adjustability of the laptop in four degrees of freedom.

Although specific features of the invention are shown in some drawings and not others, this is for convenience only, as the features can be combined as would be apparent to those skilled in the art, and as the claims set forth the rights granted under the patent. Other combinations of features would be apparent to those skilled in the field and are within the scope of the claims.

What is claimed is:

1. A laptop computer stand for holding a laptop computer, wherein the laptop computer includes a keyboard portion and a display portion, and wherein the keyboard portion includes an upper surface having a plurality of keys, a lower surface, a front, a rear, and two lateral sides, and wherein the display portion is pivotably coupled to the keyboard portion, the laptop computer stand comprising:

a base adapted to be placed on a substantially horizontal surface or coupled to a structure, and wherein the base is selectively pivotable relative to the substantially horizontal surface or the structure;

a substantially rectangular support member having a front side, a back side opposite the front side, a top edge, a bottom edge generally opposite the top edge, and first and second opposing side edges, wherein the support member is coupled to the base at the back side of the support member at a location approximately midway between the first and second opposing side edges, and where the support member is selectively pivotable relative to the base;

a pair of retainer members coupled to the bottom edge of the support member and generally perpendicular to front side of the support member and are adapted to support the keyboard portion of the laptop computer;

a pair of opposing first support structures each having a top edge, a bottom edge, and first and second opposing side edges, where each of the first support structures is coupled at its first side edge to one of the opposing side edges of the support member, and where the first support structures are generally perpendicular to the front side of the support member and are adapted to restrain the front of the keyboard portion;

a pair of second support structures, each having a top edge, a bottom edge, and first and second opposing side edges, where each of the second support structures is coupled at its first side edge to the second side edge of one of the first support structures, and where the second support structures are generally parallel to the front side of the support member, for engaging the front of the keyboard portion;

a bar coupled to the back side of the support member;

a locking mechanism mounted on the bar; and a tab insertable in the locking mechanism.

2. The laptop computer stand of claim 1, where the support member is selectively pivotable relative to the base through the use of one or more torque hinges.

* * * * *